(12) United States Patent
Yost et al.

(10) Patent No.: US 7,769,447 B2
(45) Date of Patent: Aug. 3, 2010

(54) CARDIAC PACEMAKER WITH TABLE-BASED PACING MODE IMPLEMENTATION

(75) Inventors: David W. Yost, Brooklyn Park, MN (US); Doug M. Birkholz, Shoreview, MN (US); James A. Esler, Coon Rapids, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 379 days.

(21) Appl. No.: 11/116,596

(22) Filed: Apr. 28, 2005

(65) Prior Publication Data

US 2006/0247708 A1 Nov. 2, 2006

(51) Int. Cl.
*A61N 1/08* (2006.01)
(52) U.S. Cl. .......................................... 607/9
(58) Field of Classification Search .............. 607/9
See application file for complete search history.

(56) References Cited

U.S. PATENT DOCUMENTS

| | | | |
|---|---|---|---|
| 4,378,020 A | 3/1983 | Nappholz et al. | |
| 4,407,288 A | 10/1983 | Langer et al. | |
| 4,503,857 A | 3/1985 | Boute et al. | |
| 4,554,920 A | 11/1985 | Baker, Jr. et al. | |
| 4,577,633 A | 3/1986 | Berkovits et al. | |
| 4,779,617 A | 10/1988 | Whigham | |
| 4,928,688 A | 5/1990 | Mower | |
| 5,022,395 A | 6/1991 | Russie | |
| 5,081,987 A | 1/1992 | Nigam | |
| 5,085,215 A | 2/1992 | Nappholz et al. | |
| 5,103,820 A | 4/1992 | Markowitz | |
| 5,247,930 A | 9/1993 | Begemann et al. | |
| 5,292,340 A | 3/1994 | Crosby et al. | |
| 5,312,450 A | 5/1994 | Markowitz | |
| 5,360,437 A | 11/1994 | Thompson | |
| 5,431,691 A * | 7/1995 | Snell et al. | 607/27 |
| 5,545,186 A | 8/1996 | Olson et al. | |
| 5,643,326 A | 7/1997 | Weiner et al. | |
| 5,692,907 A * | 12/1997 | Glassel et al. | 434/262 |
| 5,725,561 A | 3/1998 | Stroebel et al. | |
| 5,776,168 A | 7/1998 | Gunderson | |
| 5,792,203 A | 8/1998 | Schroeppel | |
| 5,991,659 A | 11/1999 | de Vries et al. | |
| 6,026,324 A | 2/2000 | Carlson | |
| 6,129,745 A | 10/2000 | Sun et al. | |
| 6,366,810 B1 | 4/2002 | Johnson et al. | |

(Continued)

OTHER PUBLICATIONS

Ternes, David, et al., "Flexible Neural Stimulation Engine", U.S. Appl. No. 11/550,912, filed Oct. 19, 2006, 45 pages.

(Continued)

*Primary Examiner*—Mark W Bockelman
*Assistant Examiner*—Eric D. Bertram
(74) *Attorney, Agent, or Firm*—Schwegman, Lundberg & Woessner, P.A.

(57) ABSTRACT

A device and method for implementing a bradycardia pacing mode are disclosed which is mostly hardware-based but still allows the flexibility for making major changes in brady behavior normally found only in firmware-based implementations. The brady behavior of the device is encapsulated by a table in an area of RAM referred to as brady RAM, and the brady behavior can be changed by re-loading the brady RAM with a different table.

8 Claims, 5 Drawing Sheets

U.S. PATENT DOCUMENTS

| | | |
|---|---|---|
| 6,427,084 B2 | 7/2002 | Baker et al. |
| RE38,119 E | 5/2003 | Mower |
| 6,920,355 B2 | 7/2005 | Baker et al. |
| 7,006,872 B2 | 2/2006 | Gielen et al. |
| 7,047,066 B2 | 5/2006 | Vanderlinde et al. |
| RE39,897 E | 10/2007 | Mower |
| 2007/0043398 A1 | 2/2007 | Ternes et al. |

OTHER PUBLICATIONS

Bakker, P. F., et al., "Beneficial Effects of Biventricular Pacing in Congestive Heart Failure", *PACE*, 17 (4), Part II, NASPE Abstract No. 318,(Apr. 1994),1 pg.

Gaggini, G., et al., "Mixed Microprocessor-Random Logic Approach for Innovative Pacing Systems", *Pacing and Clinical Electrophysiology*, 15 (11), (1992), 1858-1861.

Mower, M., U.S. Patent Office Patent Application Information Retrieval (PAIR) search results for U.S. Appl. No. 10/214,474, filed Aug. 8, 2002, entitled *"Method and Apparatus for Treating Hemodynamic Disfunction"*, 3 pgs.

Stotts, L. J., et al., "An 8-bit Microcomputer with Analog Subsystems for Implantable Biomedical Application", *IEEE Journal of Solid-State Circuits*, 24 (2), (1989), 292-300.

"U.S. Appl. No. 11/550,912, Examiner Interview Summary mailed Jun. 15, 2009", 2 pgs.

"U.S. Appl. No. 11/550,912, Response filed Feb. 23, 2009 to Restriction Requirement mailed Jan. 21, 2009", 9 pgs.

"U.S. Appl. No. 11/550,912, Response filed Jun. 15, 2009 to Non Final Office Action mailed Mar. 19, 2009", 12 pgs.

"U.S. Appl. No. 11/550,912, Response filed Dec. 9, 2009 to Final Office Action mailed Oct. 1, 2009", 12 pgs.

"U.S. Appl. No. 11/550,912 , Final Office Action mailed Oct. 1, 2009", 8 pgs.

\* cited by examiner

| Condition word | AVI expired 1 | VAI expired 2 | V-sense 3 | A-sense 4 | PVARP expired 5 |

| Action word | V-pace 1 | A-pace 2 | Reset AVI 3 | Reset VAI 4 | Reset PVARP 5 |

Fig. 4

CARDIAC PACEMAKER WITH TABLE-BASED PACING MODE IMPLEMENTATION

FIELD OF THE INVENTION

This invention pertains generally to the field of cardiac pacemakers and implantable cardioverter/defibrillators incorporating a pacing function. In particular, the invention relates to the hardware and software used to control the operation of such devices.

BACKGROUND

It is now common for patients having disorders of cardiac rhythm to be treated with implantable pacemakers that provide electrical stimulation to selected chambers of the heart in the form of timed pacing pulses. The most common condition for which pacemakers are used is in the treatment of bradycardia, where the ventricular rate is too slow. Atrio-ventricular conduction defects (i.e., AV block) that are permanent or intermittent and sick sinus syndrome represent the most common causes of bradycardia for which permanent pacing may be indicated. If functioning properly, the pacemaker makes up for the heart's inability to pace itself at an appropriate rhythm in order to meet metabolic demand by enforcing a minimum heart rate and/or artificially restoring AV conduction. Pacing therapy delivered in this manner is referred to as bradycardia or "brady" pacing. Particular bradycardia pacing modes determine how the pacing pulses are delivered in response to sensed cardiac events and lapsed time intervals. Pacing therapy may also be delivered using a bradycardia pacing mode for the purpose of restoring synchronous ventricular contractions in patients with inter-ventricular or intra-ventricular conduction disorders, termed cardiac resynchronization therapy.

The earliest pacemakers were hardware-based devices in which pacing decisions were made by logic circuits implemented in hardware. Most cardiac pacemakers today, however, (including implantable cardioverter/defibrillators with pacing capability) are microprocessor-based systems in which software (a.k.a. firmware, as the term is used here) run by a microprocessor commands the generation of pacing outputs, with various timers being used to alert the microprocessor as to when to pace. Such firmware-based systems exhibit great flexibility, as compared with a pacemaker implemented with dedicated hardware, since the behavior of the device can be changed simply by reprogramming the microprocessor. Controlling the delivery of paces with a firmware-based system, however, also has some disadvantages. If the microprocessor continually executes instructions during the cardiac cycle in order to process and respond to timing and sensing events, a large amount of battery power is consumed. Also, making pacing decisions with software inevitably introduces some variability into the timing of the paces, commonly referred to as pacing jitter.

SUMMARY

In the approach described herein, a bradycardia pacing mode is implemented using a brady table which maps particular device states, as defined by the occurrence of sensed events and the states of timers, to particular device actions such as the delivery of pacing pulses and the resetting or stopping of timers. Hardware-based circuitry compares the current state of the device to the device states contained in the brady table. If the current device state matches a table device state, the circuitry performs the actions to which the table device state is mapped. The brady table may be stored in an area of RAM, referred to as the brady RAM, which can be accessed by a microprocessor as well as the hardware-based circuitry. Device behavior may thus be easily changed by loading a different brady table into the brady RAM.

BRIEF DESCRIPTION OF THE DRAWINGS

FIG. 4 illustrates an example of action and condition word construction.

DETAILED DESCRIPTION

Figure 1:
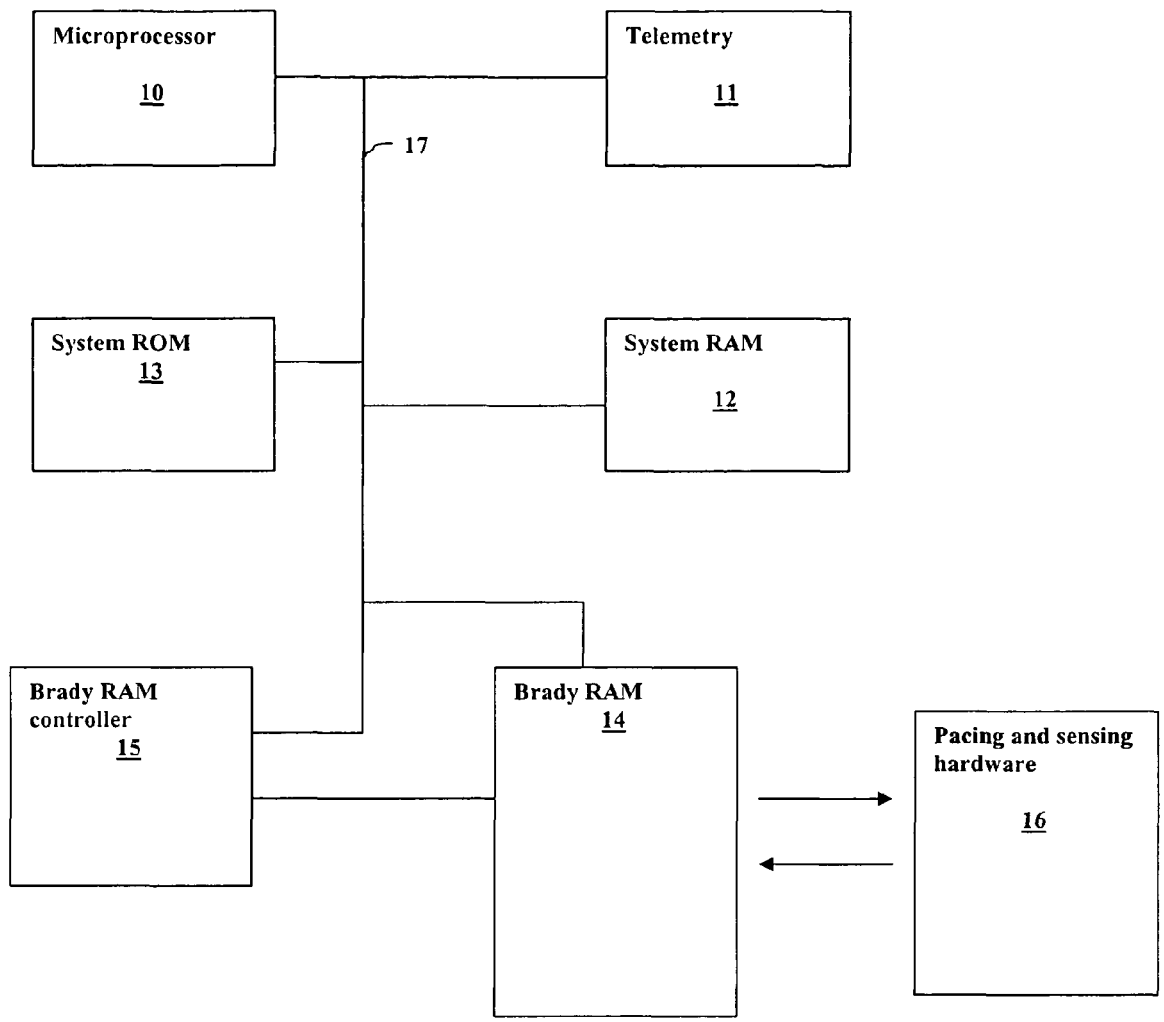
FIG. 1 is a system diagram of an implantable pacemaker.

Described herein is a device and method for implementing a bradycardia pacing mode which allows for a low power implementation that is mostly hardware-based but still allows the flexibility for making major changes in brady behavior normally found only in firmware-based implementations. The brady behavior of the device is encapsulated by a RAM-based table in an area of RAM referred to as brady RAM, and the brady behavior can be changed by re-loading the brady RAM with a different table. Firmware executed by a microprocessor may load the table based on the brady mode desired. Hardware then reads the table only when pacing decisions need to be made, and uses the information in the table to make brady decisions. The design may be easily extended to more complicated pacing modes by making the RAM larger. Because hardware rather than firmware decides when to pace, there is no latency in pace delivery, and no jitter in the cycle length. The device may also utilize a FIFO queue in an area of the brady RAM or elsewhere in which either hardware or firmware may record particular events along with a timestamp for latter retrieval and analysis. The RAM based brady table may be used to define which brady events the hardware will put in a FIFO. Firmware can also place any event in the FIFO, where such events may be unrelated to brady events. The FIFO queue eases the task of keeping events in chronological order when both hardware and firmware are recording events.

Set forth below are descriptions of an exemplary implantable device and hardware for implementing a bradycardia pacing mode in the manner just described. An exemplary implementation of a pacing mode using a brady table is also given.

1. Implantable Device Description

An implantable pacemaker includes a housing containing electronic circuitry and one or more electrodes in electrical contact with the myocardium used for sensing and pacing the heart. The housing is usually implanted subcutaneously on the patient's chest, and is connected to the electrodes by leads threaded through the vessels of the upper venous system into the heart. The electronic circuitry contained within the housing includes a battery, circuitry for generating pacing pulses, circuitry for interpreting electrogram signals representing cardiac electrical activity, and logic circuitry for operating the pacemaker in a number of programmed pacing modes where a pacing mode defines how pacing pulses are output in response to particular sensed events and the expiration of particular defined time intervals. Telemetry circuitry is usually also provided to enable communication with an external programmer that can interrogate the pacemaker and receive stored data as well as directly adjust the operating parameters of the pacemaker after implantation.

An electrode can be incorporated into a sensing channel that generates an electrogram signal representing cardiac electrical activity at the electrode site and/or incorporated into a pacing channel for delivering pacing pulses to the site. A pacing channel includes a pulse generator connected to an electrode while a sensing channel includes a sense amplifier connected to an electrode and a comparator circuit for comparing the electrogram signal to a specified threshold value. The sensing circuitry of the device generates atrial and ventricular electrogram signals from the voltages sensed by the electrodes of a particular channel. An electrogram is analogous to a surface EKG and indicates the time course and amplitude of cardiac depolarization and repolarization that occurs during either an intrinsic or paced beat. When an electrogram signal in an atrial or ventricular sensing channel exceeds a specified threshold (e.g., as determined by a comparator) the sensing circuitry detects an atrial or ventricular sense, respectively, which pacing algorithms may employ to trigger or inhibit pacing. Sensing and/or pacing channels may be configured as either atrial or ventricular channels allowing the device to deliver conventional ventricular single-site pacing with or without atrial tracking, biventricular pacing, or multi-site pacing of a single chamber.

2. Bradycardia Pacing Modes

Bradycardia pacing modes refer to pacing algorithms which are used to pace the atria and/or ventricles in a manner that enforces a certain minimum heart rate or restores AV conduction. Because of the risk of inducing an arrhythmia with asynchronous pacing, most pacemakers for treating bradycardia are programmed to operate synchronously in a so-called demand mode where sensed cardiac events occurring within a defined interval either trigger or inhibit a pacing pulse. In a triggered mode, a sense occurring in one heart chamber triggers a pace to either the same or a different heart chamber. Inhibited demand pacing modes utilize escape intervals to control pacing in accordance with sensed intrinsic activity. In an inhibited demand mode, a pacing pulse is delivered to a heart chamber during a cardiac cycle only after expiration of a defined escape interval during which no intrinsic beat by the chamber is detected. For example, a ventricular escape interval for pacing the ventricles can be defined between ventricular events, referred to as the cardiac cycle (CC) interval with its inverse being the lower rate limit or LRL. The CC interval is restarted with each ventricular sense or pace. An atrial escape interval can also be defined for pacing the atria either alone or in addition to pacing the ventricles which starts with a ventricular sense or pace and is referred to as the ventriculo-atrial interval or VAI. In atrial tracking and AV sequential pacing modes, another ventricular escape interval is defined between atrial and ventricular events, referred to as the atrio-ventricular pacing delay interval or AVI, where a ventricular pacing pulse is delivered upon expiration of the atrio-ventricular pacing delay interval if no ventricular sense occurs before. In an atrial tracking mode, the atrio-ventricular pacing delay interval is triggered by an atrial sense and stopped by a ventricular sense or pace. In an AV sequential pacing mode, the atrio-ventricular delay interval is triggered by an atrial pace and stopped by a ventricular sense or pace. Atrial tracking and AV sequential pacing are commonly combined so that an AVI starts with either an atrial pace or sense.

Cardiac resynchronization therapy is pacing stimulation applied to one or more heart chambers in a manner that compensates for conduction delays and is most conveniently delivered in conjunction with a bradycardia pacing mode. Ventricular resynchronization pacing is useful in treating heart failure in patients with interventricular or intraventricular conduction defects because, although not directly inotropic, resynchronization results in a more coordinated contraction of the ventricles with improved pumping efficiency and increased cardiac output. Ventricular resynchronization can be achieved in certain patients by pacing at a single unconventional site, such as the left ventricle instead of the right ventricle in patients with left ventricular conduction defects. Resynchronization pacing may also involve biventricular pacing with the paces to right and left ventricles delivered either simultaneously or sequentially, with the interval between the paces termed the biventricular delay (BVD) interval (also sometimes referred to as the VV delay). The BVD interval may be zero in order to pace both ventricles simultaneously, or non-zero in order to pace the left and right ventricles sequentially. In an example biventricular resynchronization pacing mode, right atrial paces and senses trigger an AVI which upon expiration results in a pace to one of the ventricles and which is stopped by a right ventricular sense. The contralateral ventricular pace is delivered at the specified BVD interval with respect to expiration of the AVI.

Another aspect of bradycardia pacing modes involves the use of timer-defined refractory periods for the sensing channels. In order to prevent cross-talk between sensing channels and other types of false sensing, certain events may cause a sensing channel to be rendered refractory for specified period time during which sensed events may be ignored for purposes of the pacing algorithm, interpreted as noise, or only used for other purposes such as tachyarrhythmia detection. A refractory period is initiated when a particular event starts a timer which defines the refractory period and is terminated upon expiration of the timer. Sensing channels are commonly rendered refractory for a period of time upon occurrence of a sense or pace in the same or different channel. One well-known example of a cross-chamber refractory period is the post-ventricular atrial refractory period or PVARP which renders the atrial sensing channel refractory for a period of time following a ventricular sense or pace in order to prevent pacemaker mediated tachycardia.

3. Electronic Circuitry for Implementing Bradycardia Pacing

FIG. 1 is a system diagram of the electronic components contained within the pacemaker housing which are used to implement a pacing mode by causing the delivery of paces in response to sensed cardiac events and lapsed time intervals. A microprocessor 10 communicates with a system RAM 12 and a system ROM 13 for containing data and programmed instructions over a bidirectional system address and data bus 17. Telemetry circuitry 11 is also interfaced to the bus enabling communication between the microprocessor and an external programmer. The microprocessor 10 controls the overall operation of the device in accordance with programmed instructions stored in memory. In most pacemaker designs being used at the present time, instructions executed by a microprocessor are also responsible for implementing the pacing mode by making pacing decisions based the outputs of timers and sensing circuitry in what may be termed a firmware-based implementation. In the presently described approach, on the other hand, the pacing algorithm is encapsulated by a brady table which maps particular device states, as defined by the occurrence of sensed events and the states of timers, to particular device actions such as the delivery of pacing pulses and the resetting or stopping of timers. Hardware-based circuitry driven by a clock signal compares the current state of the device to the device states contained in the brady table. If the current device state matches a table device state, the circuitry performs the actions to which the table device state is mapped. The brady table may be stored in an area of RAM, referred to as the brady RAM, which can also be accessed by the microprocessor. Device behavior may thus be easily changed by loading a different brady table into the brady RAM. This approach thus obtains the advantages of hardware driven pacing, namely, low power and timing stability, but offers a flexibility similar to that of firmware-based pacing implementations. FIG. 1 illustrates a brady RAM 14 and brady RAM controller 15 interfaced to the bus 17. When enabled by the microprocessor, the brady RAM controller 14 sequentially accesses the table device states and associated actions contained in the brady RAM. The brady RAM 14 is interfaced to pacing and sensing hardware 16 which includes the sensing and pacing channels of the device and hardware timers for defining escape intervals and refractory periods. Logic circuitry associated with the brady RAM 14 includes circuitry for comparing the current state of the device with the table device states and for causing the device actions contained in the brady table to be performed by the hardware 16.

Figure 2:
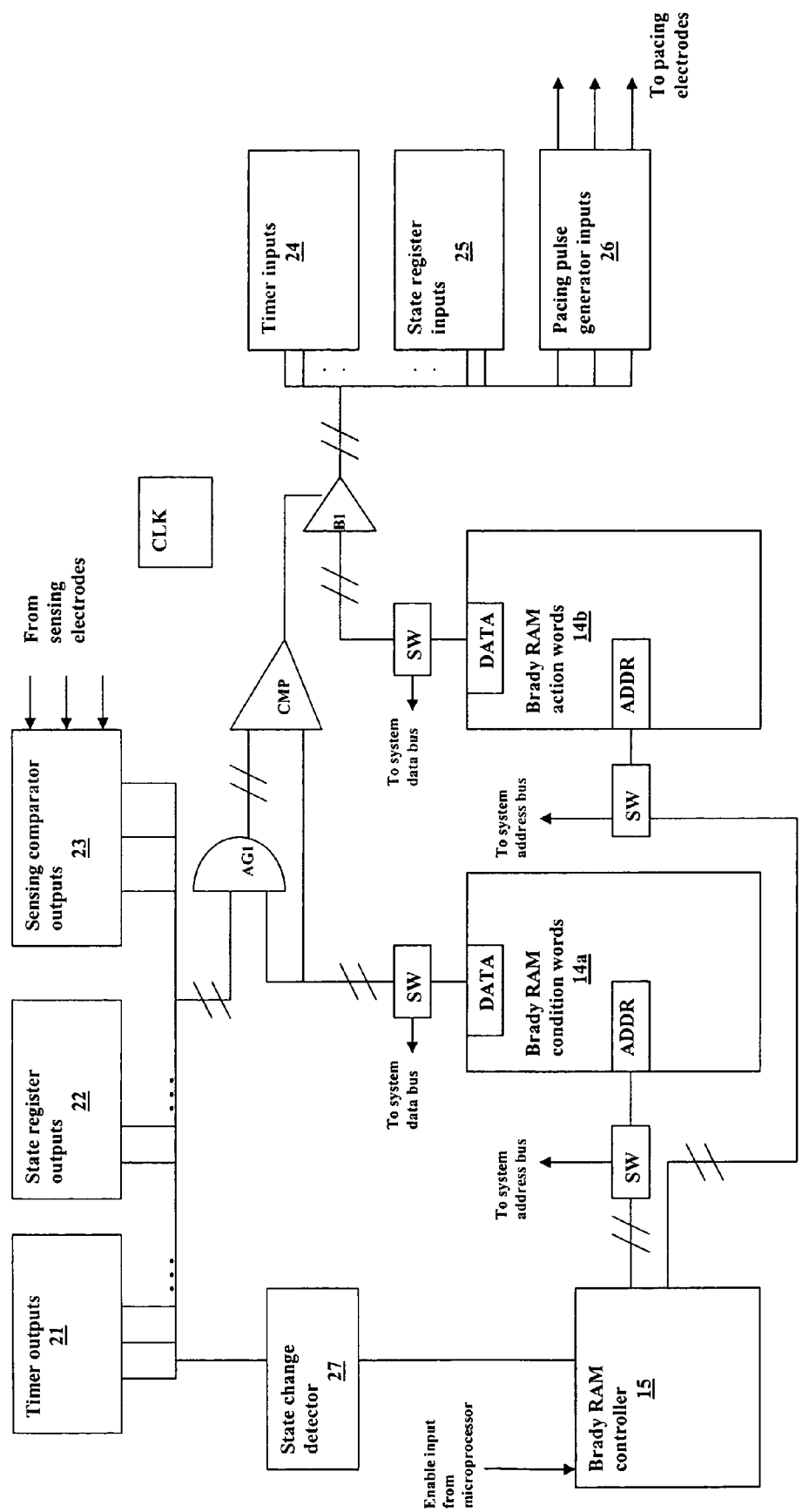
FIG. 2 illustrates hardware for implementing a pacing mode with a brady table.

FIG. 2 illustrates the operation of the brady RAM-based pacing circuitry in more detail according to one particular embodiment. The brady RAM is shown as being divided into a brady RAM 14a which contains a set of condition words and a brady RAM 14b which contains an action word corresponding to each condition word. Each condition word represents a particular device state according to whether particular bits of the word are set or cleared, and each action word represents particular actions which can be performed by the device according to whether particular bits of the word are set or cleared. In other words, each bit of a condition word may represent the state of a particular timer or whether a particular sensed event has occurred, and each bit of an action word may represent a timer input or delivery of a pace through a particular pacing channel. When enabled by the microprocessor 10, the brady RAM controller 15 accesses the brady RAM by asserting the address of a condition word to the brady RAM 14a and the address of the corresponding action word to brady RAM 14b. When the brady RAM controller 15 is enabled, the microprocessor also actuates a plurality of solid state switches SW which isolate the brady RAM 14a and 14b from the system address and data bus 17. The switches SW block the system address bus and pass the address outputs of the brady RAM controller to the brady RAM when the brady RAM controller is operating, and vice-versa when the microprocessor 10 is accessing the brady RAM. Similarly, the data bits of both brady RAM 14a and 14b are also isolated from the system data bus 17 by switches SW when the brady RAM controller is operating, and vice-versa when the microprocessor is reading or writing to the brady RAM.

The current state of the device is represented by a set of timer outputs 21 (i.e., timer states such as running, stopped, or expired), a set of state register outputs 22 which may define certain behaviors, and a set of sensing comparator outputs 23. The state register outputs may define any type of detected condition or event which can be used to affect device behavior (e.g., detection of a noisy condition in a particular sensing channel). Together, these outputs may be thought of as a current status word. The condition words in the brady RAM 14a are constructed with a bit-by-bit correspondence to the outputs of the current status word. The actions which may be taken by the device in implementing a bradycardia pacing mode are represented by a set of action inputs which may include timer inputs 24 (e.g., starting or resetting, stopping, or disabling a particular timer), a set of state register inputs 25 which cause the contents of the state registers to change, and a set of pacing pulse generator inputs 26 which cause delivery of paces to particular pacing electrodes. An action input may also be provided for causing a particular event represented in the current status word to be stored in a FIFO queue along with a time stamp. The FIFO queue may be located in the brady RAM or elsewhere. The action words in the brady RAM 14b are constructed with a bit-by-bit correspondence to the set of available action inputs.

The operation of the brady hardware starts when the brady RAM controller 15 is enabled. In this embodiment, the operation of the brady RAM controller is triggered by a change in device status. When a bit of the current status word changes as detected by state change detector 27, the brady RAM controller begins to sequence through each condition word in the brady table by sequentially asserting the address of each condition word to the brady RAM 14a and the address of the corresponding action word to brady RAM 14b. A signal derived from the system clock CLK drives the brady RAM controller at an appropriate frequency to cause the addresses of the condition and actions words to be asserted in sequence. As the address of a condition word is asserted, the data bits of the condition word are output from the brady RAM 14a. In this embodiment, a set bit (i.e., a one) in the condition word signifies a particular timer state or sensing comparator output which defines a particular device state, and a cleared bit (i.e., a zero) signifies that a particular timer state or sensing comparator output does not matter in defining the particular device state. In order to evaluate whether a device state defined by a condition word matches the current device state, the condition word is passed to a multi-bit AND gate AG1 where the condition word is ANDed with the current status word. The output of the gate AG1 is then compared with the condition word by a multi-bit comparator CMP. If the condition word represents the current state of the device, the output of comparator CMP is asserted which enables the multi-bit buffer B1. The data bits of the corresponding action word in the brady RAM 14b which are addressed by the brady RAM controller are then passed to the set of action inputs to cause the actions specified by the action word. After all of the condition words are evaluated in this manner, the brady RAM controller waits for another change in the device state and then repeats the sequence.

4. Example Pacing Mode Implementation

The brady RAM-based circuitry described above may be configured to implement any pacing mode where paces are delivered in accordance with defined timer states and sensed events. By way of example, what follows is a description of a simplified atrial and ventricular pacing mode and how that pacing mode is implemented in the brady RAM as condition words and corresponding action words.

Figure 3:
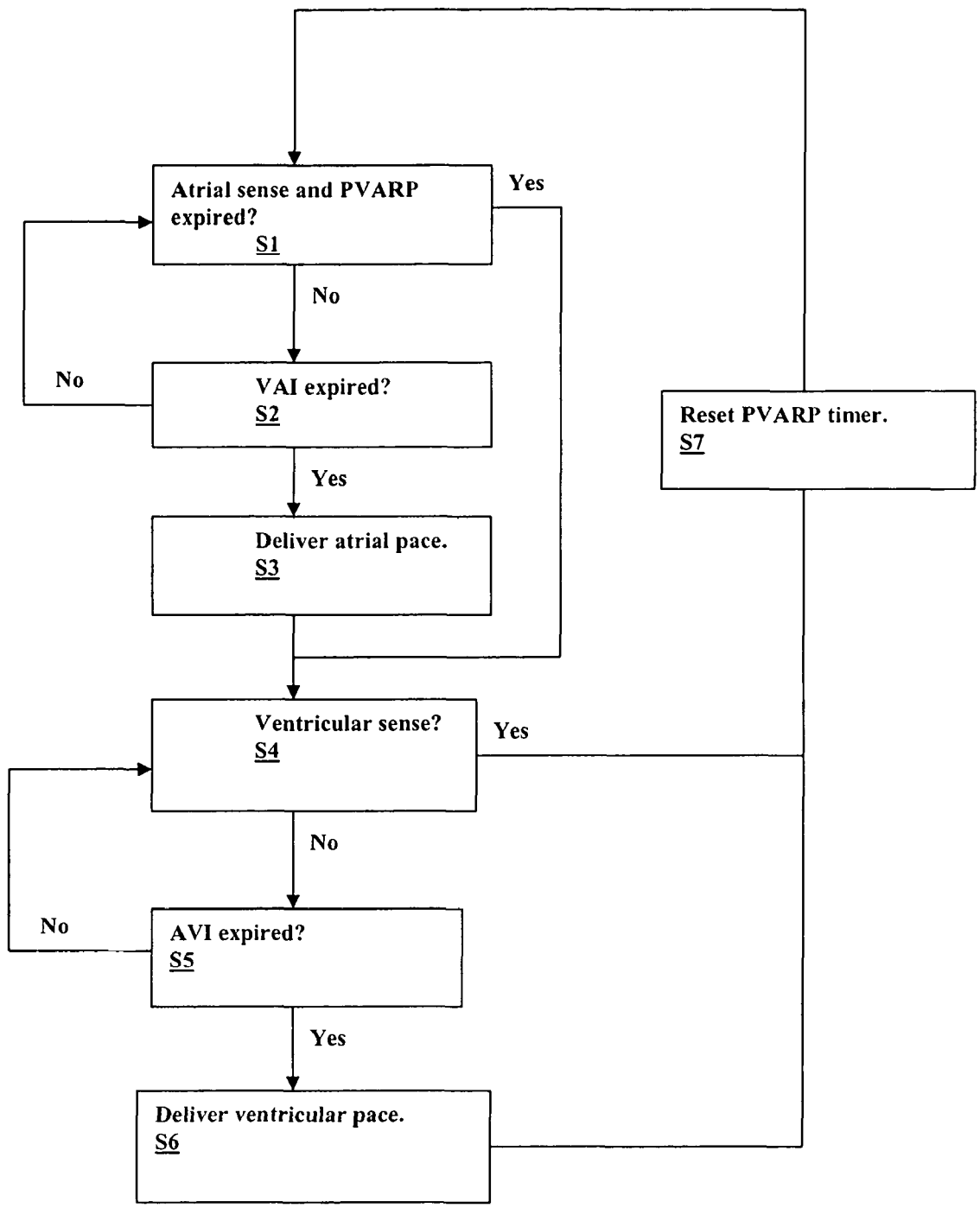
FIG. 3 illustrates an exemplary bradycardia pacing mode.

FIG. 3 illustrates a particular DDD pacing algorithm as steps S1 through S7. Two escape intervals are defined: an AVI started by an atrial sense or pace which upon expiration results in a ventricular pace, and a VAI started by a ventricular sense or pace which upon expiration results in an atrial pace. Only one refractory period is defined, a PVARP, which is started by a ventricular sense or pace and which renders the atrial sensing channel refractory for its duration.

FIG. 4 shows how the timer states, sensed events, and device actions of the pacing algorithm illustrated by FIG. 3 are encoded as condition words and action words. A condition word has five bits numbered 1 through 5 which, if set, represent AVI expiration, VAI expiration, a ventricular sense, an atrial sense, and PVARP expiration, respectively. An action word also has five bits numbered 1 through 5 which, if set, represent a ventricular pace, an atrial pace, resetting (i.e., restarting) the AVI, resetting the VAI, and resetting the PVARP, respectively.

Figure 5:
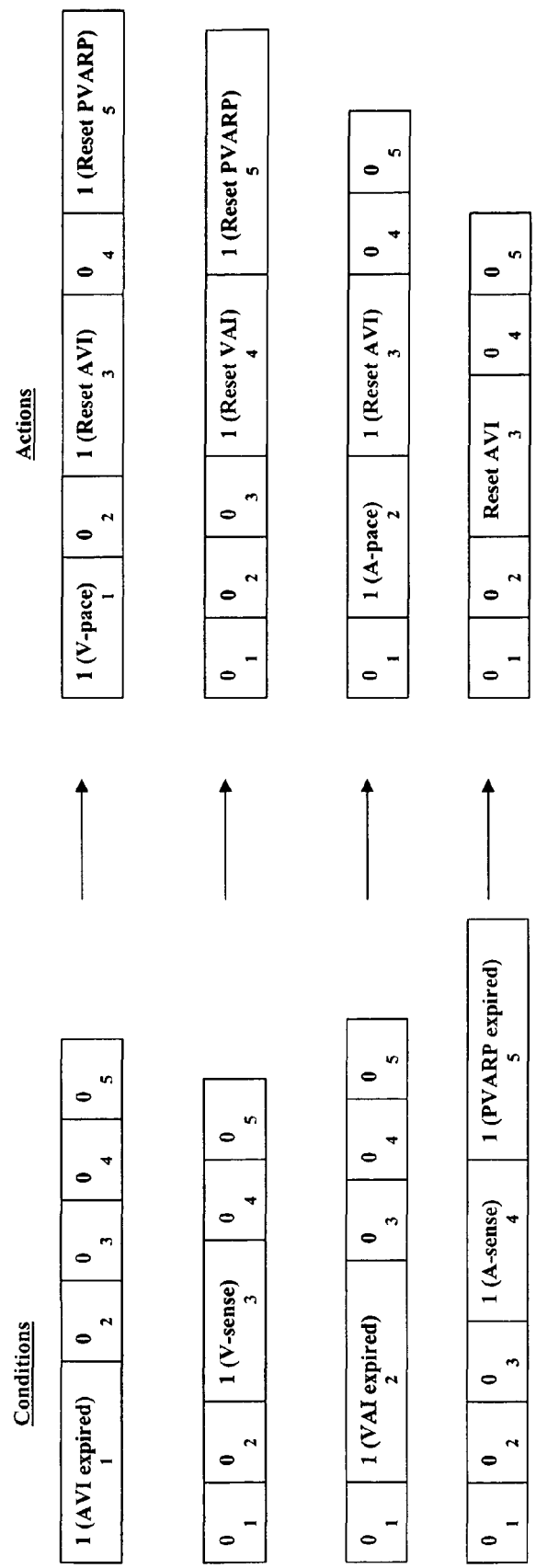
FIG. 5 illustrates exemplary action and condition word pairs for implementing a bradycardia pacing mode.

FIG. 5 shows how different condition words may be associated with different action words in a brady table in order to implement the pacing algorithm illustrated by FIG. 3. The implementation requires four condition/action word pairs which map different device states to different device actions. The first pair results in a ventricular pace being delivered if the AVI is expired regardless of what else is included in the current status word. The VAI and PVARP are also reset. The second pair causes resetting of the VAI and PVARP when a ventricular sense occurs. The third pair causes delivery of an atrial pace and resetting of the AVI when the VAI expires. The fourth pair shows that an atrial sense causes resetting of the AVI only if the PVARP is also expired. This latter behavior may alternatively be interpreted as not generating an atrial sense if the PVARP is unexpired.

Although the invention has been described in conjunction with the foregoing specific embodiments, many alternatives, variations, and modifications will be apparent to those of ordinary skill in the art. Such alternatives, variations, and modifications are intended to fall within the scope of the following appended claims.

What is claimed is:

1. A cardiac pacemaker, comprising:
   sensing circuitry for sensing an electrogram signal from an electrode adapted for disposition at a cardiac location generating a sensed event when the electrogram signal exceeds a specified threshold;
   pacing circuitry for delivering a pacing pulse to a pacing electrode adapted for disposition at a cardiac location;
   a brady RAM containing a brady table which maps particular device states defined by timer states and/or sensed events to associated device actions which include pacing pulse delivery and/or changes in timer states;
   wherein the brady table is made up of condition words representing particular device states and corresponding action words representing particular device actions;
   one or more timers, state registers, and sensing comparators whose outputs define a current status word that represents the current operating state of the device; and,
   a brady RAM controller configured to sequentially assert addresses of the condition words and corresponding action words in the brady table on an address bus to cause the data bits of an addressed condition word and the corresponding action word to be output from the brady RAM;
   a multi-bit comparator for comparing the data bits of each sequentially addressed condition word with the current status word; and
   a multi-bit buffer that, when enabled by an output from the multi-bit comparator when a condition word is found that matches the current status word, passes the data bits of the corresponding action word to a set of action inputs to cause actions specified by the action word.

2. The pacemaker of claim 1 further comprising:
   a microprocessor; and,
   system address and data buses through which the microprocessor may access the brady RAM.

3. The pacemaker of claim 2 further comprising switches for isolating the brady RAM from the system address and data buses when the brady RAM controller is accessing the brady RAM.

4. The pacemaker of claim 1 wherein the action inputs specified by the action word are selected from timer inputs, state register inputs, and pulse generator inputs.

5. The pacemaker of claim 4 wherein the action inputs specified by the action word include an action input for causing a particular event represented in the current status word to be stored in a FIFO queue along with a time stamp.

6. The pacemaker of claim 1 further comprising a state change detector for detecting changes in the current status word and, when a bit of the current status word changes, trigger the brady RAM controller to begin sequencing through each condition word in the brady table by sequentially asserting the address of each condition word and the address of the corresponding action word to the brady RAM.

7. The pacemaker of claim 1 further comprising a multi-bit AND gate for ANDing the current status word with the condition word in the brady RAM addressed by the brady RAM controller and whose output is compared with the addressed condition word by the comparator.

8. The pacemaker of claim 1 wherein a state register output signifies detection of a noisy condition in a particular sensing channel.

* * * * *